(12) United States Patent
Dwyer et al.

(10) Patent No.: US 6,743,219 B1
(45) Date of Patent: Jun. 1, 2004

(54) DELIVERY APPARATUS FOR A SELF-EXPANDING STENT

(75) Inventors: Clifford J. Dwyer, Weston, FL (US);
Luis A. Davila, Pleasanton, CA (US);
Frederick Feller, III, Margate, FL (US); Mark L. Mathis, Fremont, CA (US); David J. Wilson, Ft. Lauderdale, FL (US)

(73) Assignee: Cordis Corporation, Miami Lakes, FL (US)

( * ) Notice: Subject to any disclaimer, the term of this patent is extended or adjusted under 35 U.S.C. 154(b) by 105 days.

(21) Appl. No.: 09/631,002

(22) Filed: Aug. 2, 2000

(51) Int. Cl.[7] ............................................. A61M 25/00
(52) U.S. Cl. ..................... 604/525; 623/1.11; 606/108
(58) Field of Search ................................ 606/108, 200, 606/151, 191, 192, 194, 195, 198; 623/1.11, 1.23; 604/93.01, 104, 506–510, 264, 271, 523–530

(56) References Cited

U.S. PATENT DOCUMENTS

| | | |
|---|---|---|
| 4,580,568 A | 4/1986 | Gianturco |
| 4,649,922 A | 3/1987 | Wiktor |
| 4,699,611 A | 10/1987 | Bowden |
| 4,732,152 A | 3/1988 | Wallsten et al. |
| 4,733,665 A | 3/1988 | Palmaz |
| 4,739,762 A | 4/1988 | Palmaz |
| 4,771,773 A | 9/1988 | Kropf |
| 4,776,337 A | 10/1988 | Palmaz |
| 4,830,003 A | 5/1989 | Wolff et al. |
| 4,913,141 A | 4/1990 | Hillstead |
| 5,007,914 A | 4/1991 | Schweigerling |
| 5,019,085 A | 5/1991 | Hillstead |
| 5,026,377 A | 6/1991 | Burton et al. |
| 5,037,427 A | 8/1991 | Harada et al. |
| 5,078,720 A | 1/1992 | Burton et al. |
| 5,201,757 A | 4/1993 | Heyn et al. |
| 5,342,300 A | 8/1994 | Stefanadis et al. |
| 5,344,426 A | 9/1994 | Lau et al. |
| 5,372,600 A | 12/1994 | Beyar et al. |
| 5,391,172 A | 2/1995 | Williams et al. |
| 5,407,432 A | 4/1995 | Solar |
| 5,409,495 A | 4/1995 | Osborn |
| 5,411,507 A | 5/1995 | Heckele |
| 5,415,664 A | 5/1995 | Pinchuk |
| 5,443,477 A | 8/1995 | Marin et al. |

(List continued on next page.)

FOREIGN PATENT DOCUMENTS

| | | |
|---|---|---|
| EP | 1 025 813 A2 | 9/2000 |
| WO | WO 96/32078 A1 | 10/1996 |

OTHER PUBLICATIONS

European Search Report dated Dec. 16, 2003 for corresponding Appln. No. 01 03 6602.
International Search Report dated Jun. 12, 2003 for corresponding application No. PCT/US02/19203.

*Primary Examiner*—David J. Isabella
*Assistant Examiner*—Urmi Chattopadhyay

(57) ABSTRACT

A delivery apparatus for self-expanding stents may be utilized to safely deliver stents to a target site. The apparatus has an outer sheath forming an elongated tubular member having distal and proximal ends and an inside and outside diameter. The apparatus also includes an inner shaft located coaxially within the outer sheath. The inner shaft has a distal end, a proximal end and a longitudinal axis extending therebetween. At least a portion of the inner shaft is made from a flexible coiled member. The shaft preferably includes a stop attached thereto, the stop being proximal to the distal end of the sheath. Lastly, the apparatus includes a self-expanding stent located within the outer sheath, wherein the stent makes frictional contact with the outer sheath and the shaft is disposed coaxially within a lumen of the stent. During deployment of the stent, the stent makes contact with the stop.

25 Claims, 4 Drawing Sheets

U.S. PATENT DOCUMENTS

| | | |
|---|---|---|
| 5,453,090 A | 9/1995 | Martinez et al. |
| 5,456,694 A | 10/1995 | Marin et al. |
| 5,458,615 A | 10/1995 | Klemm et al. |
| 5,464,408 A | 11/1995 | Duc |
| 5,464,449 A | 11/1995 | Ryan et al. |
| 5,476,505 A | 12/1995 | Limon |
| 5,478,349 A | 12/1995 | Nicholas |
| 5,480,423 A | 1/1996 | Ravenscroft et al. |
| 5,484,444 A | 1/1996 | Braunschweiler et al. |
| 5,507,768 A | 4/1996 | Lau et al. |
| 5,507,770 A | 4/1996 | Turk |
| 5,522,883 A | 6/1996 | Slater et al. |
| 5,534,007 A | 7/1996 | St. Germain et al. |
| 5,540,712 A | 7/1996 | Kleshinski et al. |
| 5,545,209 A | 8/1996 | Roberts et al. |
| 5,569,296 A | 10/1996 | Marin et al. |
| 5,571,114 A | 11/1996 | Devanaboyina |
| 5,571,135 A | 11/1996 | Fraser et al. |
| 5,571,168 A | 11/1996 | Toro |
| 5,591,196 A | 1/1997 | Marin et al. |
| 5,591,197 A | 1/1997 | Orth et al. |
| 5,591,226 A | 1/1997 | Trerotola et al. |
| 5,593,412 A | 1/1997 | Martinez et al. |
| 5,601,600 A | 2/1997 | Ton |
| 5,603,698 A | 2/1997 | Roberts et al. |
| 5,607,466 A | 3/1997 | Imbert et al. |
| 5,618,300 A | 4/1997 | Marin et al. |
| 5,628,754 A | 5/1997 | Shevlin et al. |
| 5,643,278 A | 7/1997 | Wijay |
| 5,669,880 A | 9/1997 | Solar |
| 5,683,451 A | 11/1997 | Lenker et al. |
| 5,690,643 A | 11/1997 | Wijay |
| 5,690,644 A | 11/1997 | Yurek et al. |
| 5,695,498 A | 12/1997 | Tower |
| 5,697,948 A | 12/1997 | Marin et al. |
| 5,702,418 A | 12/1997 | Ravenscroft |
| 5,707,376 A | 1/1998 | Kavteladze et al. |
| 5,709,701 A | 1/1998 | Parodi |
| 5,709,703 A | 1/1998 | Lukic et al. |
| 5,713,907 A | 2/1998 | Hogendijk et al. |
| 5,733,267 A | 3/1998 | Del Toro |
| 5,735,859 A | 4/1998 | Fischell et al. |
| 5,746,763 A | 5/1998 | Benderev et al. |
| 5,746,765 A | 5/1998 | Kleshinski et al. |
| 5,749,880 A | 5/1998 | Banas et al. |
| 5,755,722 A | 5/1998 | Barry et al. |
| 5,772,669 A | 6/1998 | Vrba |
| 5,776,140 A | 7/1998 | Cottone |
| 5,776,141 A | 7/1998 | Klein et al. |
| 5,776,142 A | 7/1998 | Gunderson |
| 5,782,855 A | 7/1998 | Lau et al. |
| 5,788,707 A | 8/1998 | Del Toro et al. |
| 5,792,144 A | 8/1998 | Fischell et al. |
| 5,800,517 A | 9/1998 | Anderson et al. |
| 5,810,871 A | 9/1998 | Tuckey et al. |
| 5,814,062 A | 9/1998 | Sepetka et al. |
| 5,824,036 A | 10/1998 | Lauterjung |
| 5,824,055 A | 10/1998 | Spiridigliozzi et al. |
| 5,836,965 A | 11/1998 | Jendersee et al. |
| 5,836,967 A | 11/1998 | Schneider |
| 5,843,090 A | 12/1998 | Schuetz |
| 5,843,092 A | 12/1998 | Heller et al. |
| 5,846,247 A | 12/1998 | Unsworth et al. |
| 5,851,210 A | 12/1998 | Torossian |
| 5,860,998 A | 1/1999 | Robinson et al. |
| 5,868,755 A | 2/1999 | Kanner et al. |
| 5,873,906 A | 2/1999 | Lau et al. |
| 5,879,324 A | 3/1999 | von Hoffmann |
| 5,891,154 A | 4/1999 | Loeffler |
| 5,893,867 A | 4/1999 | Bagaoisan et al. |
| 5,902,317 A | 5/1999 | Kleshinski et al. |
| 5,902,333 A | 5/1999 | Roberts et al. |
| 5,906,619 A | 5/1999 | Olson et al. |
| 5,910,145 A | 6/1999 | Fischell et al. |
| 5,911,715 A | 6/1999 | Berg et al. |
| 5,919,204 A | 7/1999 | Lukic et al. |
| 5,919,225 A | 7/1999 | Lau et al. |
| 5,928,246 A | 7/1999 | Gordon et al. |
| 5,928,248 A | 7/1999 | Acker |
| 5,944,726 A | 8/1999 | Blaeser et al. |
| 5,951,569 A | 9/1999 | Tuckey et al. |
| 5,957,930 A | 9/1999 | Vrba |
| 5,968,052 A | 10/1999 | Sullivan et al. |
| 5,968,053 A | 10/1999 | Revelas |
| 5,976,153 A | 11/1999 | Fischell et al. |
| 5,980,530 A | 11/1999 | Willard et al. |
| 5,980,533 A | 11/1999 | Holman |
| 5,989,280 A | 11/1999 | Euteneuer et al. |
| 6,004,328 A | 12/1999 | Solar |
| 6,004,347 A | 12/1999 | McNamara et al. |
| 6,007,543 A | 12/1999 | Ellis et al. |
| 6,015,429 A | 1/2000 | Lau et al. |
| 6,019,777 A | 2/2000 | Mackenzie |
| 6,019,778 A | 2/2000 | Wilson et al. |
| 6,027,510 A | 2/2000 | Alt |
| 6,033,413 A | 3/2000 | Mikus et al. |
| 6,042,588 A | 3/2000 | Munsinger et al. |
| 6,045,557 A | 4/2000 | White et al. |
| 6,068,634 A | 5/2000 | Lorentzen Cornelius et al. |
| 6,070,589 A | 6/2000 | Keith et al. |
| 6,077,273 A | 6/2000 | Euteneuer et al. |
| 6,077,295 A | 6/2000 | Limon et al. |
| 6,093,194 A | 7/2000 | Mikus et al. |
| 6,096,027 A | 8/2000 | Layne |
| 6,096,045 A | 8/2000 | Del Toro et al. |
| 6,106,530 A | 8/2000 | Harada |
| 6,108,886 A | 8/2000 | Kimes et al. |
| 6,113,608 A | 9/2000 | Monroe et al. |
| 6,117,140 A | 9/2000 | Munsinger |
| 6,120,522 A | 9/2000 | Vrba et al. |
| 6,123,720 A | 9/2000 | Anderson et al. |
| 6,123,723 A | 9/2000 | Konya et al. |
| 6,126,685 A | 10/2000 | Lenker et al. |
| 6,132,471 A | 10/2000 | Johlin, Jr. |
| 6,136,006 A | 10/2000 | Johnson et al. |
| 6,136,011 A | 10/2000 | Stambaugh |
| 6,139,572 A | 10/2000 | Campbell et al. |
| 6,143,016 A | 11/2000 | Bleam et al. |
| 6,143,021 A | 11/2000 | Staehle |
| 6,146,389 A | 11/2000 | Geitz |
| 6,146,415 A | 11/2000 | Fitz |
| 6,152,944 A | 11/2000 | Holman et al. |
| 6,159,229 A | 12/2000 | Jendersee et al. |
| 6,162,231 A | 12/2000 | Mikus et al. |
| 6,168,617 B1 | 1/2001 | Blaeser et al. |
| 6,174,316 B1 | 1/2001 | Tuckey et al. |
| 6,174,327 B1 | 1/2001 | Mertens et al. |
| 6,183,481 B1 | 2/2001 | Lee et al. |
| 6,186,978 B1 * | 2/2001 | Samson et al. .......... 604/96.01 |
| 6,190,393 B1 | 2/2001 | Bevier et al. |
| 6,193,727 B1 | 2/2001 | Foreman et al. |
| 6,196,230 B1 | 3/2001 | Hall et al. |
| 6,200,337 B1 | 3/2001 | Moriuchi et al. |
| 6,203,558 B1 | 3/2001 | Dusbabek et al. |
| 6,206,888 B1 | 3/2001 | Bicek et al. |
| 6,217,585 B1 | 4/2001 | Houser et al. |
| 6,217,586 B1 | 4/2001 | Mackenzie |
| 6,383,171 B1 * | 5/2002 | Gifford et al. .............. 604/508 |

* cited by examiner

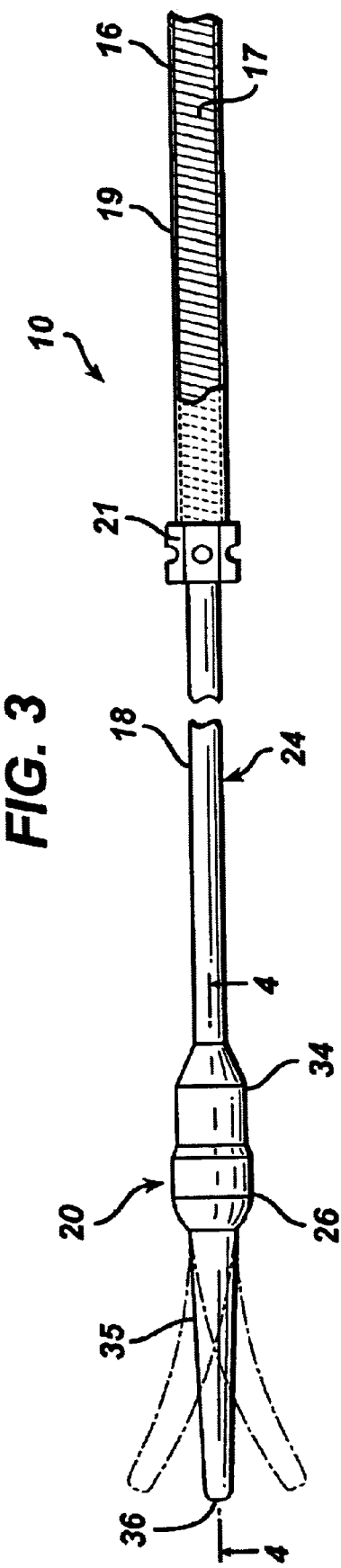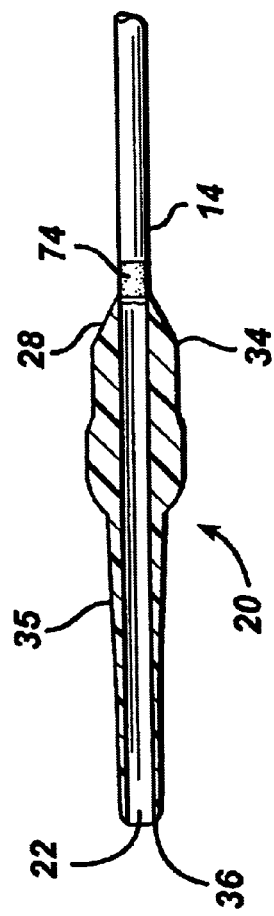

DELIVERY APPARATUS FOR A SELF-EXPANDING STENT

FIELD OF THE INVENTION

The present invention relates to expandable intraluminal grafts ("stents") use within a body passageway or duct which are particularly useful for pairing blood vessels narrowed or occluded by disease. The present invention relates even further to systems for delivering such stents.

BACKGROUND OF THE INVENTION

Various endoprosthesis assemblies which include expandable stents have been proposed or developed for use in association with angioplasty treatments and other medical procedures. The endoprosthesis assembly is percutaneously routed to a treatment site and the stent is expanded to maintain or restore the patency of a body passageway such as a blood vessel or bile duct. A stent is typically cylindrical in shape comprising an expandable open frame. The stent will typically expand either by itself (self-expanding stents) or will expand upon exertion of an outwardly directed radial force on an inner surface of the stent frame by a balloon catheter or the like.

Stents for endovascular implantation into a blood vessel or the like to maintain or restore the patency of the passageway have been deployed percutaneously to minimize the invasiveness associated with surgical exposure of the treatment site during coronary artery bypass. Percutaneous deployment is initiated by an incision into the vascular system of the patient, typically into the femoral artery. A tubular or sheath portion of an introducer is inserted through the incision and extends into the artery. The introducer has a central lumen which provides a passageway through the patient's skin and artery wall into the interior of the artery. An outwardly tapered hub portion of the introducer remains outside the patient's body to prevent blood from leaking out of the artery along the outside of the sheath. The introducer lumen includes a valve to block blood flow out of the artery through the introducer passageway. A distal end of a guide wire is passed through the introducer passageway into the patient's vasculature. The guide wire is threaded through the vasculature until the inserted distal end extends just beyond the treatment site. The proximal end of the guide wire extends outside the introducer.

For endovascular deployment, a stent, in an unexpanded or constricted configuration, is crimped onto a deflated balloon portion of a balloon catheter. The balloon portion is normally disposed near a distal end of the balloon catheter. The catheter has a central lumen extending its entire length. The distal end of the balloon catheter is threaded onto the proximal end of the guide wire. The distal end of the catheter is inserted into the introducer lumen and the catheter is pushed along the guide wire until the stent reaches the treatment site. At the treatment site, the balloon is inflated causing the stent to radially expand and assume an expanded configuration. When the stent is used to reinforce a portion of the blood vessel wall, the stent is expanded such that its outer diameter is approximately 10% to 20% larger than the inner diameter of the blood vessel at the treatment site, effectively causing an interference fit between the stent and the blood vessel that inhibits migration of the stent. The balloon is deflated and the balloon catheter is withdrawn from the patient's body. The guide wire is similarly removed. Finally, the introducer is removed from the artery.

An example of a commonly used stent is given in U.S. Pat. No. 4,733,665 filed by Palmaz on Nov. 7, 1985, which is incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly extending force.

However, such "balloon expandable" stents are often impractical for use in some vessels such as superficial arteries, like the carotid artery. The carotid artery is easily accessible from the exterior of the human body, and is often visible by looking at ones neck. A patient having a balloon expandable stent made from stainless steel or the like, placed in their carotid artery might be susceptible to sever injury through day to day activity. A sufficient force placed on the patients neck, such as by falling, could cause the stent to collapse, resulting in injury to the patient. In order to prevent this, self expanding stents have been proposed for use in such vessels. Self expanding stents act like springs and will recover to their expanded or implanted configuration after being crushed.

One type of self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprisesan outer catheter for holding the stent at its distal end, and an inner piston which pushes the stent forward once it is in position.

Other types of self-expanding stents use alloys such as Nitinol (Ni—Ti alloy), which have shape memory and/or superelastic characteristics. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increasesin stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

Designing delivery systems for delivering self-expanding stents has proven difficult. One example of a prior art self-expanding stent delivery system is shown in U.S. Pat. No. 4,580,568 issued to Gianturco on Apr. 8, 1986. This reference discloses a delivery apparatus which uses a hollow sheath, like a catheter. The sheath is inserted into a body vessel and navigated therethrough so that its distal end is adjacent the target site. The stent is then compressed to a smaller diameter and loaded into the sheath at the sheath's proximal end. A cylindrical flat end pusher, having a diameter almost equal to the inside diameter of the sheath is inserted into the sheath behind the stent. The pusher is then used to push the stent from the proximal end of the sheath to the distal end of the sheath. Once the stent is at the distal end of the sheath, the sheath is pulled back, while the pusher remain stationary, thereby exposing the stent and allowing it to expand within the vessel.

However, delivering the stent through the entire length of the catheter can cause many problems, including possible damage to a vessel or the stent during its travel. In addition, it is often difficult to design a pusher having enough flexibility to navigate through the catheter, but also enough stiffness to push the stent out of the catheter. Therefore, it was discovered that pre-loading the stent into the distal and of the catheter, and then delivering the catheter through the vessel to the target site may be a better approach. In order to ensure proper placement of the stent within catheter, it is often preferred that the stent be pre-loaded at the manufacturing site. Except this in itself has posed some problems. Because the catheter exerts a significant force on the self expanding stent which keeps it from expanding, the stent may tend to become imbedded within the inner wall of the catheter. When this happens, the catheter has difficulty sliding over the stent during delivery. This situation can result in the stent becoming stuck inside the catheter, or could damage the stent during delivery.

Another example of a prior art self-expanding stent delivery system is given in U.S. Pat. No. 4,732,152 issued to Wallsten et al. on Mar. 22, 1988. This patent discloses a probe or catheter having a self-expanding stent pre-loaded into its distal end. The stent is first placed within a flexible hose and compressed before it is loaded into the catheter. When the stent is at the delivery site the catheter and hose are withdrawn over the stent so that it can expand within the vessel. However, withdrawing the flexible hose over the stent during expansion could also cause damage to the stent.

An example of a more preferred self-expanding stent delivery system can be found in U.S. Pat. No. 6,019,778 issued to Wilson et al. on Feb. 1, 2000, which is incorporated herein by reference. It is essential for the stent delivery device to be able to navigate through tortuous vessels, lesions and previously deployed devices (stents). The delivery system must follow a guide wire with out overpowering the wire in the tortuous vessels. The guidewire when entering a new path will needs to be flexible enough to bend such that it is angled with respect to the delivery device proximal thereto. Because the guidewire extends through the distal end of the delivery device, if the distal end of the delivery device is stiff, it will not bend with the guidewire and may prolapse the wire causing the guidewire to move its position to align itself with the distal end of the delivery device. This could cause difficulty in navigating the delivery system, and may also cause any debris dislodged during the procedure to flow upstream and cause a stroke.

Therefore, there has been a need for a self-expanding stent delivery system which better navigates tortuous passageways, and more accurately deploys the stent within the target area. The present invention provides such a delivery device.

SUMMARY OF THE INVENTION

In accordance with the present invention, there is provided a delivery apparatus for a self-expanding stent. The apparatus has an outer sheath forming an elongated tubular member having distal and proximal ends and an inside and outside diameter. The apparatus also includes an inner shaft located coaxially within the outer sheath. The inner shaft has a distal end, a proximal end and a longitudinal axis extending therebetween. At least a portion of the inner shaft is made from a flexible coiled member. The shaft preferably includes a stop attached thereto, the stop being proximal to the distal end of the sheath. Lastly, the apparatus includes a self-expanding stent located within the outer sheath, wherein the stent makes frictional contact with the outer sheath and the shaft is disposed coaxially within a lumen of the stent. During deployment of the stent, the stent makes contact with the stop.

BRIEF DESCRIPTION OF DRAWINGS

The foregoing and other aspects of the present invention will best be appreciated with reference to the detailed description of the invention in conjunction with the accompanying drawings, wherein:

FIG. 3 is a simplified elevational view of the distal end of the inner shaft made in accordance with the present invention.

FIG. 4 is a cross-sectional view of FIG. 3 taken along lines 4—4.

DETAILED DESCRIPTION OF THE INVENTION

Figure 1:
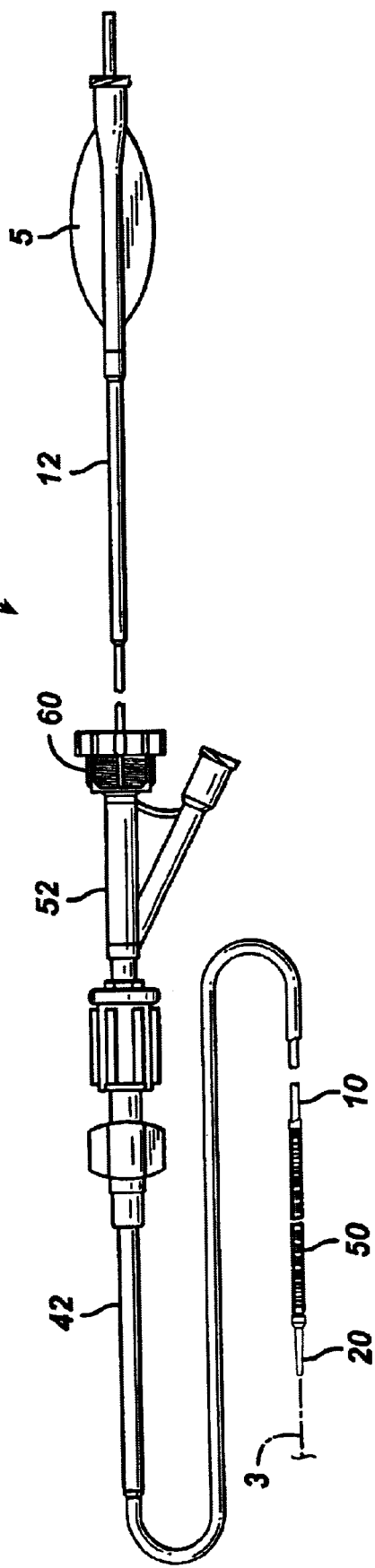
FIG. 1 is a simplified elevational view of a stent delivery apparatus made in accordance with the present invention.
Figure 2:
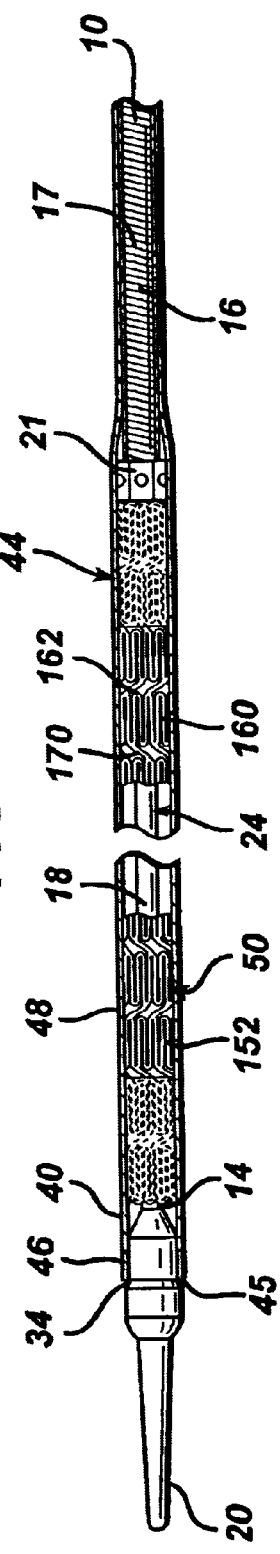
FIG. 2 is a view similar to that of FIG. 1 but showing an enlarged view of the distal end of the apparatus having a section cut away to show the stent loaded therein.

Referring now to the figures wherein like numerals indicate the same element throughout the views, there is shown in FIGS. 1 and 2 a self-expanding stent delivery apparatus 1 made in accordance with the present invention. Apparatus 1 comprises inner and outer coaxial tubes. The inner tube is called the shaft 10 and the outer tube is called the sheath 40. A self-expanding stent 50 is located within the outer sheath 40, wherein the stent 50 makes frictional contact with the outer sheath 40 and the shaft 10 is disposed coaxially within a lumen of the stent 50.

Shaft 10 has proximal and distal ends 12 and 14 respectively. The proximal end 12 of the shaft has a Luer guidewire hub 5 attached thereto. As seen best from FIG. 10, proximal end 12 is preferably a ground stainless steel hypotube. In one exemplary embodiment, the hypotube is stainless steel and has a 0.042 inch outside diameter at its proximal end and then tapers to a 0.036 inch outside diameter at its distal end. The inside diameter of the hypotube is 0.032 inch throughout its length. The tapered outside diameter is to gradually change the stiffness of the hypo tube along its length. This change in the hypotube stiffness allows for a more rigid proximal end or handle end that is needed during stent deployment. If the proximal end is not stiff enough the hypotube section extending beyond the valve could buckle as the deployment forces are transmitted. The distal end of the hypotube is more flexible allowing for better trackability in tortuous vessels. The distal end of the hypo also needs to be flexible to minimize the transition between the hypo and the coil section.

As will be described in greater detail below, shaft 10 has a body portion 16, wherein at least a section of body portion 16 is made from a flexible coiled member 17, looking very much like a compressed or closed coil spring. Shaft 10 also includes a distal portion 18, distal to body 16, which is preferably made from a coextrusion of high density polyethylene and nylon. The two portions 16 and 18 are joined together by any number of means known to those of ordinary skill in the art including heat fusing, adhesive bonding, chemical bonding or mechanical attachment.

As best seen from FIG. 3, the distal portion 14 of the shaft 10 has a distal tip 20 attached thereto. Distal tip 20 can be made from any number of materials known in the art including polyamide, polyurethane, polytetrafluoroethylene, and polyethylene including multi-layer or single layer structures. The distal tip 20 has a proximal end 34 whose diameter is substantially the same as the outer diameter of the sheath 40 which is immediately adjacent thereto. The distal tip 20 tapers to a smaller diameter from its proximal end 34 to its distal end 36, wherein the distal end 36 of the distal tip 20 has a diameter smaller than the inner diameter of the sheath 40.

The delivery device 1 glides over a guide wire 3 (shown in FIG. 1) during navigation to the stent deployment site. As used herein, guidewire can also refer to similar guiding devices which have a distal protection apparatus incorporated herein. One preferred distal protection device is disclosed in published PCT Application Ser. No. 98/33443, having an international filing date of Feb. 3, 1998, which is incorporated herein by reference. As discussed above, if the distal tip 20 is too stiff it will overpower the guide wire path and push the guide wire against the lumen wall and in some very tortuous setting the delivery device could prolapse the wire. Overpowering of the wire and pushing of the device against the lumen wall can prevent the device from reaching the target area because the guide wire will no longer be directing the device. Also as the device is advanced and pushed against the lumen wall debris from the lesion can be dislodged and travel upstream causing complications to distal vessel lumens. The distal tip 20 is designed with an extremely flexible leading edge and a gradual transition to a less flexible portion. The distal tip 20 can be hollow and can be made of any number of materials, including 40D nylon. Its flexibility can changed by gradually increasing the thickness of its cross-sectional diameter, whereby the diameter is thinnest at its distal end, and is thickest at its proximal end. That is, the cross-sectional diameter and wall thickness of the tip increases as you move in the proximal direction. This gives the distal end 30 of the tip 20 the ability to be directed by the guidewire 3 prior to the larger diameter and thicker wall thickness (less flexible portion) of the tip 20 overpowering the guidewire 3. Over-powering the wire 3 is when the device (due to its stiffness) dictates the direction of the device instead of following the wire.

The guidewire lumen 22 has a diameter that is matched to hug the recommended size guide wire 3 so that there is a slight frictional engagement between the guidewire 3 and the guidewire lumen 22 of tip 20. The tip 20 then has a rounded section 26 between its distal portion 36 and its proximal portion 34. This helps prevent the sheath 40 from slipping distally over the tip 20, and thereby exposing the squared edges of the sheath to the vessel, which could cause damage thereto. This improves the devices "pushability". As the tip 20 encounters resistance it does not allow the outer sheath 40 to ride over it exposing the outer sheath 40 square cut edge. Instead, the outer sheath 40 contacts the rounded section 26 of the tip 20 and thus transmits the forces applied to the tip 20. The tip 20 also has a proximally tapered section 35 which helps guide the tip 20 through the deployed stent without providing a sharp edge that could grab or hang up on a stent strut end or other irregularity in the lumen inner diameter.

Attached to distal portion 18 of shaft 10 is a stop 21 which is proximal to the distal tip 20 and stent 50. Stop 21 can be made from any number of materials known in the art, including stainless steel, and is even more preferably made from a highly radio-opaque material such as platinum, gold, tantalum, or radio-opaque filled polymer. The stop 21 can be attached to shaft 10 by mechanical or adhesive bonding, or by any other means known to those skilled in the art. Preferably, the diameter of stop 21 is large enough to make sufficient contact with the loaded stent 50 without making frictional contact with the outer sheath 40. As will be explained later herein, stop 21 helps to "push" the stent 50 or maintain its relative position during deployment, by preventing the stent 50 from migrating proximally within the sheath 40 during retraction of the sheath 40 for stent 50 deployment. The radio-opaque stop 21 also aides in positioning the stent 50 within the target lesion during deployment within a vessel, as is described below.

A stent bed 24 is defined as being that portion of the shaft 10 between the distal tip 20 and the stop 21 (FIG. 2). The stent bed 24 and the stent 50 are coaxial so that the portion of shaft 18 comprising the stent bed 24 is located within the lumen of stent 50. The stent bed 24 makes minimal contact with stent 50 because of the space which exists between the inner shaft 10 and the outer sheath 40. As the stent 50 is subjected to temperatures at the austenite phase transformation it attempts to recover to its programmed shape by moving outwardly in a radial direction within the sheath. The outer sheath 40 constrains the stent 50 as will be explained later herein. Distal to the distal end of the loaded stent 50 attached to the inner shaft 10 is a radio-opaque marker 74 which can be made of platinum, iridium coated platinum, gold, tantalum, stainless steel, radiopaque filled polymer or any other suitable material known in the art.

Figure 10:
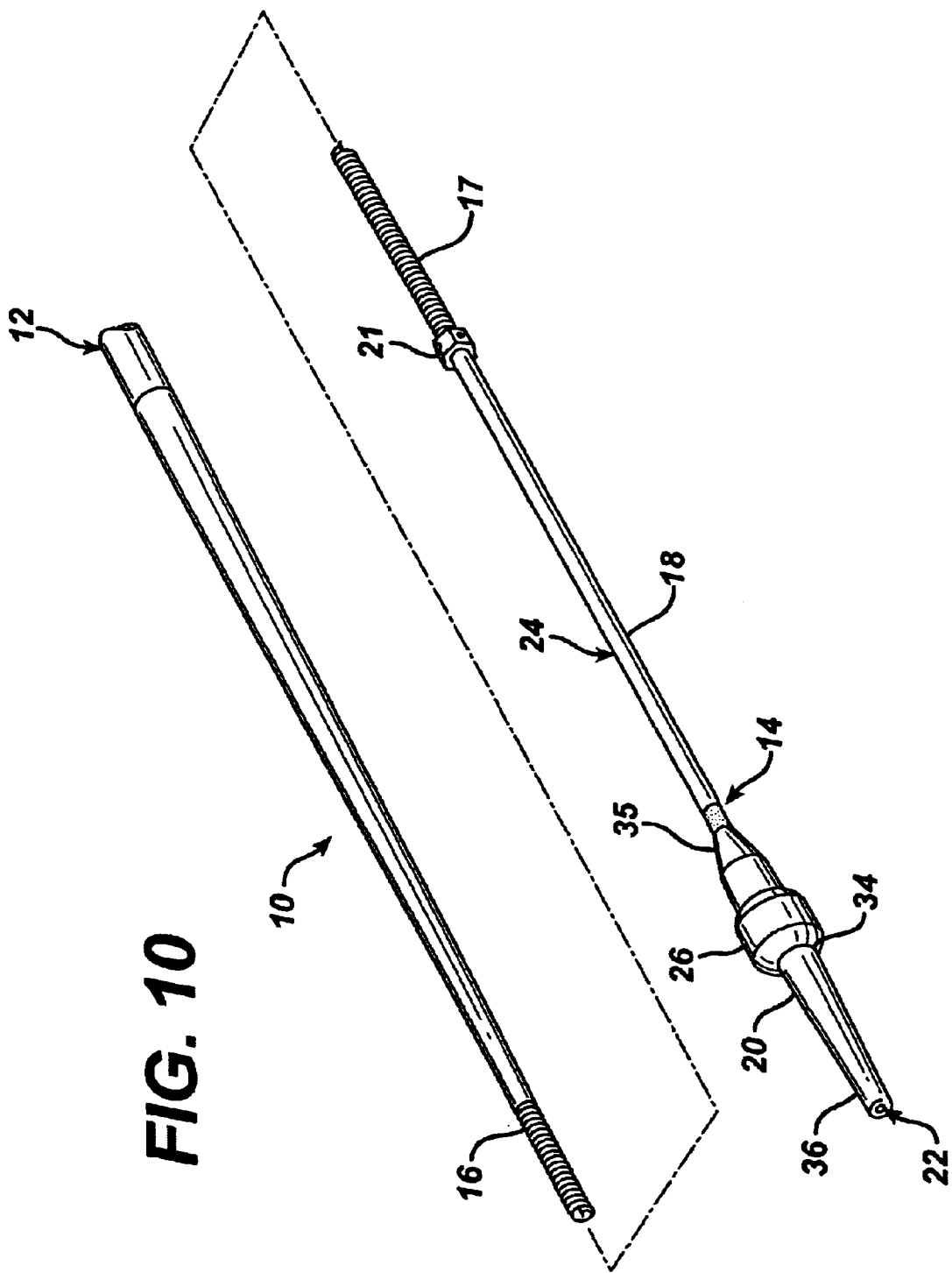
FIG. 10 is a simplified elevational view of a shaft for a stent delivery apparatus made in accordance with the present invention.

As seen from FIGS. 2, 3 and 10 the body portion 16 of shaft 10 is made from a flexible coiled member 17, similar to a closed coil or compressed spring. During deployment of the stent 50, the transmission of compression forces from the stop 21 to the hub 5 are important factors in deployment accuracy. The more compressive the construction of the inner member is, the less accurate the deployment becomes, because the compression of the inner member is not taken into account when visualizing the stent under fluoroscopic imaging. However, a less compressive shaft usually means less flexibility, which would reduce the ability of the apparatus to navigate through tortuous vessels. A coiled assembly allows both flexibility and resistance to compression. When the system is navigating through the arteries the inner member is not in compression and therefore the coil is free to bend with the delivery path. As you deploy the stent you apply tension to the outer member as you retract the outer member over the encapsulated stent. Because the stent is self-expanding it is in contact with the outer member and the forces are transferred along the stent and to the stop of the inner member. This results in the inner member being under compressive forces. When this happens, the closed coil, (no gaps between the coil members) transfers the compressive force from one coil member to the next.

The coiled member 17 further includes a covering 19 that fits over the member to help resist buckling of the coil in both bending and compressive modes. The covering 19 is an extruded polymer tube and is preferably a soft material that can elongate slightly to accommodate bending of the coil, but does not allow the coil members to ride over each other. Cover 19 can be made from any number of suitable materials including coextrusions of Nylon and high density polyethylene, polyurethane, polyamide, polytetrafluoroethylene, etc. The extrusion is also attached to the stop 21. Coil 17 can be made of any number of materials known in the art including stainless steel, Nitinol, rigid polymers. In one embodiment, coiled member 17 is made from a 0.003 inch thick by 0.010 inch wide stainless steel ribbon wire (flat wire).

Sheath 40 is preferably a polymeric catheter and has a proximal end 42 terminating at a Luer hub 52 (FIG. 1). Sheath 40 also has a distal end 45 which terminates at the proximal end 34 of distal tip 20 of the shaft 10, when the stent 50 is in un-deployed position as shown in FIG. 2 . The distal end 45 of sheath 40 includes a radio-opaque marker band 46 disposed along its outer surface (FIG. 1 and 3). As will be explained below, the stent is fully deployed when the marker band 46 is proximal to radio-opaque stop 21, thus indicating to the physician that it is now safe to remove the apparatus 1 from the body.

As detailed in FIG. 2, the distal end 45 of sheath 40 includes an enlarged section 44. Enlarged section 44 has larger inside and outside diameters than the inside and outside diameters of the sheath proximal to section 44. Enlarged section 44 houses the pre-loaded stent 50, the stop 21 and the stent bed 24. The outer sheath 40 tapers proximally at the proximal end of section 44 to a smaller size diameter. This design is better described in co-pending U.S. application Ser. No. 09/243,750 filed on Feb. 3, 1999, which is incorporated herein by reference. One particular advantage to this the reduction in the size of the outer diameter of sheath 40 proximal to enlarged section 44 results in an increase in the clearance between the delivery device 1 and the guiding catheter or sheath that the delivery device is placed through. Using fluoroscopy, the physician will view an image of the target site within the vessel, before and after deployment of the stent, by injecting a radiopaque solution through the guiding catheter or sheath with the delivery device 1 placed within the guiding catheter. Because the clearance between the outer sheath 40, and the guiding catheter is increased by tapering or reducing the outer diameter of the sheath proximal to section 44, higher injection rates are achieved, resulting in better images of the target site for the physician. The tapering of sheath 40 provides higher injection rates of radiopaque fluid, both before and after deployment of the stent.

Often self-expanding delivery systems had problems with the stent becoming embedded within the sheath or catheter in which it is disposed. Sheath 40 preferably comprises an outer polymer layer, preferably nylon, and an inner polymer layer, preferably polytetrafluoroethylene. Other suitable polymers for the inner and outer layers include any suitable material known to those skilled in the art including polyethylene, or polyamide, respectively. Preferably, positioned between outer and inner layers respectively, is a wire reinforcing layer which is preferably a braided wire made from stainless steel. An example of a self expanding stent delivery device having this type of sheath design can be found in the hereinbefore incorporated U.S. Pat. No. 6,019,778 issued to Wilson et al. on Feb. 1, 2000. The use of braiding reinforcing layers in other types of medical devices can be found in U.S. Pat. No. 3,585,707 issued to Stevens on Jun. 22, 1971, 5,045,072 issued to Castillo et al. on Sep. 3, 1991, and 5,254,107 issued to Soltesz on Oct. 19, 1993. The inclusion of a braid wire into the outer sheath enhances stent 50 deployment by helping to prevent the stent 50 from becoming too imbedded into sheath 40, prior to stent deployment.

FIGS. 1 and 2 show the stent 50 as being in its fully un-deployed position. This is the position the stent is in when the apparatus 1 is inserted into the vasculature and its distal end is navigated to a target site. Stent 50 is disposed around the stent bed 24 and at the distal end 45 of sheath 40. The distal tip 20 of the shaft 10 is distal to the distal end 45 of the sheath 40. The stent 50 is in a compressed state and makes frictional contact with the inner surface 48 of the sheath 40.

When being inserted into a patient, sheath 40 and shaft 10 are locked together at their proximal ends by a Tuohy Borst valve 60. This prevents any sliding movement between the shaft and sheath which could result in a premature deployment or partial deployment of the stent. When the stent 50 reaches its target site and is ready for deployment, the Tuohy Borst valve 60 is opened so that the sheath 40 and shaft 10 are no longer locked together.

Figure 5:
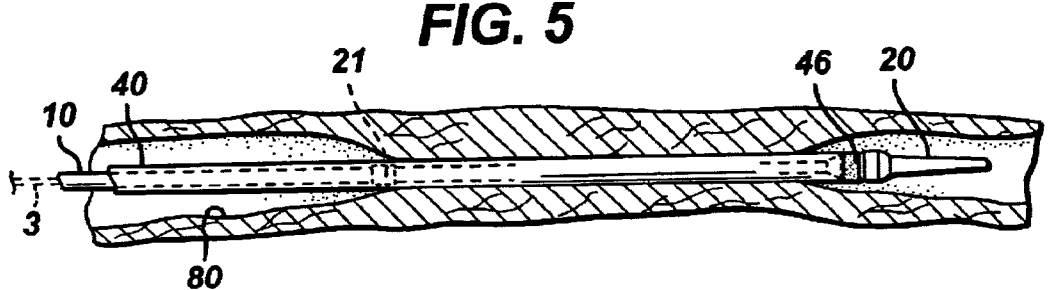
FIGS. 5 through 9 are partial cross-sectional views of the apparatus of the resent invention sequentially showing the deployment of the self expanding stent within the vasculature.
Figure 6:
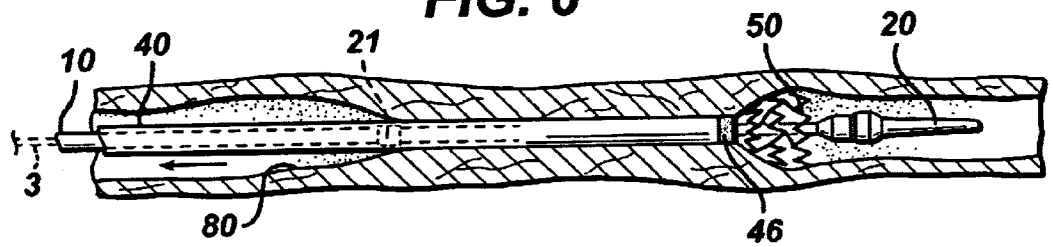
Figure 7:
Figure 8:
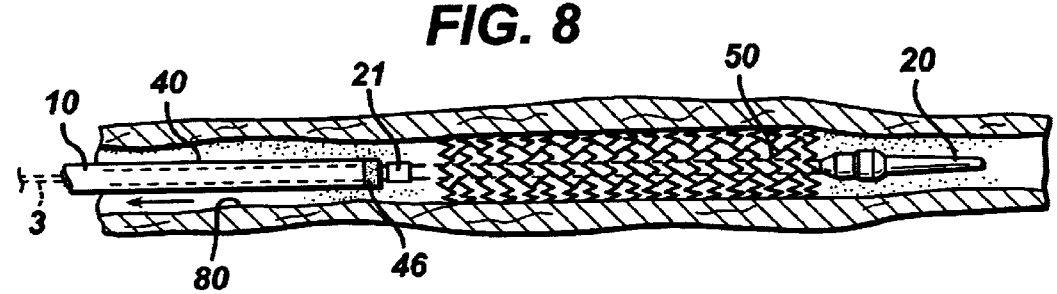

The method under which apparatus 1 deploys stent 50 can best be described by referring to FIGS. 5–9. In FIG. 5, the apparatus 1 has been inserted into a vessel 80 so that so that the stent bed 24 is at a target diseased site. Once the physician determines that the distal marker 74 and proximal marker/stop 21 on shaft 10 indicating the ends of stent 50 are sufficiently placed about the target disease site, the physician would open Tuohy Borst valve 60. The physician would then grasp the proximal end 12 or proximal hub 5 of shaft 10 so as to hold shaft 10 in a fixed position. Thereafter, the physician would grasp the Tuohy valve 60 attached proximally to outer sheath 40 and slide it proximal, relative to the shaft 10 as shown in FIGS. 6 and 7. Stop 21 prevents the stent 50 from sliding back with sheath 40, so that as the sheath 40 is moved back, the stent 50 is effectively "pushed" out of the distal end 45, or held in position relative to the target site. Stent 50 should be deployed in a distal to proximal direction to minimize the potential for creating emboli with the diseased vessel 80. Stent deployment is complete when the radio-opaque band 46 on the sheath 40 is proximal to radio-opaque stop 21, as shown in FIG. 8. The apparatus 1 can now be withdrawn through stent 50 and removed from the patient.

Figure 9:
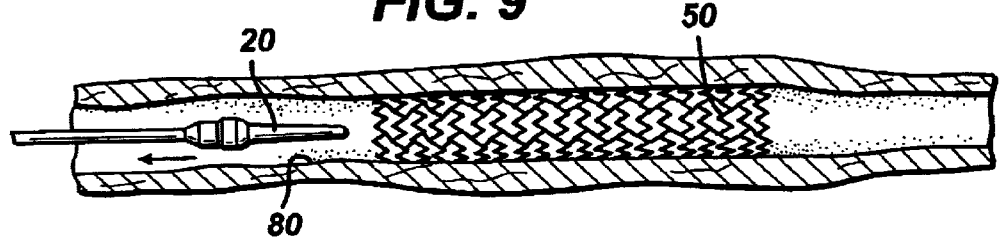

FIGS. 2 and 9 show a preferred embodiment of a stent 50 which can be used with the present invention. Stent 50 is shown in its un-expanded compressed state, before it is deployed, in FIG. 2. Stent 50 is preferably made from a superelastic alloy such as Nitinol. Most preferably, stent 50 is made from an alloy comprising from about 50.5% (as used herein these percentages refer to atomic percentages) Ni to about 60% Ni, and most preferably about 55% Ni, with the remainder of the alloy Ti. Preferably, the stent is such that it is superelastic at body temperature, and preferably has an Af in the range from about 21° C. to about 37° C. The superelastic design of the stent makes it crush recoverable which, as discussed above, can be used as a stent or frame for any number of vascular devices for different applications.

Stent 50 is a tubular member having front and back open ends a longitudinal axis extending there between. The tubular member has a first smaller diameter, FIG. 2, for insertion into a patient and navigation through the vessels, and a second larger diameter for deployment into the target area of a vessel. The tubular member is made from a plurality of adjacent hoops 152 extending between the front and back ends. The hoops 152 include a plurality of longitudinal struts 160 and a plurality of loops 162 connecting adjacent struts, wherein adjacent struts are connected at opposite ends so as to form an S or Z shape pattern. Stent 50 further includes a plurality of curved bridges 170 which connect adjacent hoops 152. Bridges 170 connect adjacent struts together at bridge to loop connection points which are offset from the center of a loop.

The above described geometry helps to better distribute strain throughout the stent, prevents metal to metal contact when the stent is bent, and minimizes the opening size between the features, struts, loops and bridges. The number of and nature of the design of the struts, loops and bridges are important factors when determining the working properties and fatigue life properties of the stent. Preferably, each hoop has between 24 to 36 or more struts. Preferably the stent has a ratio of number of struts per hoop to strut length (in inches) which is greater than 200. The length of a strut is measured in its compressed state parallel to the longitudinal axis of the stent.

In trying to minimize the maximum strain experienced by features, the stent utilizes structural geometry's which distribute strain to areas of the stent which are less susceptible to failure than others. For example, one vulnerable area of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge to loop connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and it's ability to trap embolic material.

Although particular embodiments of the present invention have been shown and described, modification may be made to the device and/or method without departing from the spirit and scope of the present invention. The terms used in describing the invention are used in their descriptive sense and not as terms of limitations.

What is claimed is:

1. A delivery apparatus for a self-expanding stent, said apparatus comprising:
   a. an outer sheath comprising an elongated tubular member having distal and proximal ends; and
   b. an inner shaft, defining a longitudinal axis, located coaxially within said outer sheath, said shaft having a distal portion and a distal end and a proximal portion and a proximal end, said inner shaft further including a body portion between said distal portion and said proximal portion, said body portion being formed from a flexible coiled member capable of stretching and compressing along said longitudinal axis said distal portion and said proximal portion being formed from non-coiled members.

2. The delivery apparatus of claim 1, wherein said coiled member is made from stainless steel.

3. The delivery apparatus of claim 1, wherein said coiled member is made from a nickel-titanium alloy.

4. The delivery apparatus of claim 1 wherein said outer sheath comprises an outer polymeric layer, an inner polymeric layer, and a wire reinforcing layer between said inner and outer layers, said reinforcing layer being more rigid than said inner and outer layers.

5. The delivery apparatus of claim 1, wherein said distal end of said shaft extends distal to said distal end of said sheath, and said proximal end of said shaft extends proximal to said proximal end of said sheath.

6. The apparatus of claim 1 wherein said sheath has an increasing durometer along its length from its distal end to its proximal end.

7. A delivery apparatus for expanding stent, said apparatus comprising:
   a. an outer sheath comprising an elongated tubular member having distal and proximal ends and an inside and outside diameter;
   b. an inner shaft, defining a longitudinal axis, located coaxially within said outer sheath, said shaft having a distal portion and a distal end and a proximal portion and a proximal end, said inner shaft further including a body portion between said distal portion and said proximal portion, said body portion being formed from a flexible coiled member capable of stretching and compressing along said longitudinal axis, said distal portion and said proximal portion being formed from non-coiled members, said shaft further including a stop attached thereto, said stop being proximal to said distal end of said sheath; and c. a self-expanding stent located within said outer sheath, said stent making frictional contact with said outer sheath, said shaft disposed coaxially within a lumen of said stent, whereby said stent makes contact with said stop during deployment of said stent.

8. The delivery apparatus of claim 7, wherein said coiled member is made from stainless steel.

9. The delivery apparatus of claim 7, wherein said coiled member is made from a nickel-titanium alloy.

10. The delivery apparatus of claim 7 wherein said outer sheath comprises an outer polymeric layer, an inner polymeric layer, and a wire reinforcing layer between said inner and outer layers, said reinforcing layer being more rigid than said inner and outer layers.

11. The delivery apparatus of claim 7, wherein said distal end of said shaft extends distal to said distal end of said sheath, and said proximal end of said shaft extends proximal to said proximal end of said sheath.

12. The apparatus of claim 7 wherein said stop makes substantially no frictional contact with said outer sheath.

13. The apparatus of claim 7 wherein said stent is made from a superelastic nickel-titanium alloy.

14. The apparatus of claim 7 wherein said shaft further includes a distal tip, said distal tip has a proximal end having an outer diameter which is not less than an outer diameter of said sheath.

15. The apparatus of claim 14 wherein said distal tip is radiopaque.

16. The apparatus of claim 7 wherein said stop is radiopaque.

17. The apparatus of claim 7 wherein said sheath has an increasing durometer along its length from its distal end to its proximal end.

18. A delivery apparatus for a self-expanding stent, said apparatus comprising:
   a. an outer sheath comprising an elongated tubular member having distal and proximal ends and an inside and outside diameter;
   b. an inner shaft, defining a longitudinal axis, located coaxially within said outer sheath, said shaft having a distal portion and a distal end and a proximal portion and a proximal end, said inner shaft further including a body portion between said distal portion and said proximal portion, said body portion being formed from a flexible coiled member capable of stretching and compressing along said longitudinal axis, said distal portion and said proximal portion being formed from non-coiled members, said coiled member having a thin layer covering on an exterior thereof, said shaft further including a stop attached thereto, said stop being proximal to said distal end of said sheath; and
   c. a self-expanding stent located within said outer sheath, said stent making frictional contact with said outer sheath, said shaft disposed coaxially within a lumen of said stent, whereby said stent makes contact with said stop during deployment of said stent.

19. The delivery apparatus of claim 18, wherein said coiled member is made from stainless steel.

20. The delivery apparatus of claim 18, wherein said thin layer covering is a polymer.

21. The delivery apparatus of claim 18 wherein said outer sheath comprises an outer polymeric layer, an inner polymeric layer, and a wire reinforcing layer between said inner and outer layers, said reinforcing layer being more rigid than said inner and outer layers.

22. The delivery apparatus of claim 18, wherein said distal end of said shaft extends distal to said distal end of said sheath, and said proximal end of said shaft extends proximal to said proximal end of said sheath.

23. The apparatus of claim 18 wherein said stent is made from a superelastic nickel-titanium alloy.

24. The apparatus of claim 18 wherein said shaft further includes a distal tip, said distal tip has a proximal end having an outer diameter which is not less than an outer diameter of said sheath.

25. The apparatus of claim 18 wherein said sheath has an increasing durometer along its length from its distal end to its proximal end.

* * * * *